(12) United States Patent
Brandt et al.

(10) Patent No.: US 6,306,283 B1
(45) Date of Patent: Oct. 23, 2001

(54) METHOD FOR SCREENING CHEMICAL SENSITIZERS

(75) Inventors: E. Steven Brandt, Rochester; Brian P. Cleary, Webster; Roger Lok, Rochester; Weimar W. White, Canaseraga, all of NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/184,200

(22) Filed: Nov. 2, 1998

(51) Int. Cl.$^7$ .................................................. G01N 27/26
(52) U.S. Cl. ...................... 205/775; 205/789; 205/789.5
(58) Field of Search ................................ 205/775, 789.5, 205/790, 789

(56) References Cited

U.S. PATENT DOCUMENTS

| | | | |
|---|---|---|---|
| 4,725,339 | * 2/1988 | Bindra et al. | 205/789.5 |
| 5,049,485 | 9/1991 | Deaton . | |
| 5,391,270 | * 2/1995 | Gui et al. | 205/789.5 |
| 5,620,841 | 4/1997 | Lok et al. . | |
| 5,700,631 | 12/1997 | Lok et al. . | |

OTHER PUBLICATIONS

Kolthoff et al, "Polarography", (1952) Month unavailable, pp. 501–502.*
Bard and Faulkner, "Electrochemical Methods," John Wiley and sons, New York (1980) Month unavailable, p. 308.
Hillson and Adam, "On Latent Images of Gold and Silver," The Journal of Photographic Science, vol. 23, p. 104 (1975) Month unavailable.
M. Suss, Chr. Schroter, J. Reinhold, H. Zwanziger, and E. Hoyer, "Gold Sensitization of Silver Bromide Layers in Polyvinyl Alcohol on Glass," J. Signal AM 5 (1997) Month unavailable.
J. Hartung, Chr. Schroter, J. Reinhold, H. Zwanziger, W. Dietzsch, and E. Hoyer, "Chemical Sensitization of Photographic Silver Bromide–Polyvinyl Alcohol Emulsions with Gold(I) Complexes of Sulfur or Phosphorus–Containing Ligands," J. Signal AM 58 (1980) Month unavailable.

* cited by examiner

*Primary Examiner*—T. Tung
(74) *Attorney, Agent, or Firm*—Sarah Meeks Roberts

(57) ABSTRACT

A method of screening a water soluble gold complex for use as a sensitizer in a silver halide photographic element comprised of experimentally measuring the electrochemical potential of the gold complex and then determining if the electrochemical potential falls within a predetermined utility window.

10 Claims, No Drawings

METHOD FOR SCREENING CHEMICAL SENSITIZERS

FIELD OF THE INVENTION

This invention relates to a method for screening gold chemical sensitizers for their use in silver halide photographic elements. The method utilizes the electrochemical reduction potentials of the sensitizers as the screening criteria.

BACKGROUND OF THE INVENTION

It is well known in photographic science that the sensitometric performance of silver halide microcrystals can be altered by so-called "chemical sensitizers." Operationally, the function of this special class of photographic addenda is to decrease the number of photons required to create a development center (i.e., increase photographic speed), independent of wavelength.

For most applications, chemical sensitizers are compounds which incorporate sulfur and/or gold into silver halides during emulsion making and/or finishing. Until relatively recently gold sensitization was frequently combined with sulfur sensitization through the use of formulations often based on aurous dithiosulfate [e.g., $Na_3Au(S_2O_3)_2$ 2 $H_2O$]. However, during the past decade the discovery and synthesis of various "gold-only" Au(I) sensitizers, such as described in U.S. Pat. Nos. 5,049,485; 5,700,631; and 5,620,841, has led to increased flexibility of chemical sensitization and increased control of components introduced into photographic makes.

Promising gold-only sensitizers are Au(I) complexes with relatively labile ligands, but without active sensitizing sulfur. Historically, the syntheses of suitable gold-only sensitizers has been difficult for a variety of reasons. Frequently, the materials compounded are either too insoluble to make an aqueous "doctor" solution or their aqueous solutions are too unstable and degrade rapidly upon keeping. Other materials, for example, some Au(I) complexes, i.e., KAu$(CN)_2$ and some Au(I) phosphino complexes, have good solution stabilities, but are so stable that emulsions prepared with them do not exhibit speed enhancement.

Because of the complexity of photographic chemistry in general and the minute quantities of silver and/or gold necessary to create a development center, little is known of the incorporated gold species which is formed during chemical sensitization. One of the explanations proposed for photographic enhancement by gold sensitization is based on the observation that silver is plated onto a gold electrode surface at a less negative potential than is silver deposited onto a silver electrode. In the electrochemical literature this phenomenon is known as "underpotential deposition" (or UPD) and has been observed for a variety of electrode metals and metal-ion combinations (Bard and Faulkner, "Electrochemical Methods," John Wiley and Sons, New York (1980), p. 308).

In the chemical sensitization mechanism, UPD of silver onto Au(0) which has been deposited onto the surface of the silver halide microcrystal would theoretically accelerate development and/or render otherwise subdevelopable latent images developable. Either route would produce an increase in photographic speed (Hillson and Adam, "On Latent Images of Gold and Silver," *J. Photogr. Sci,* 23, 104 (1975)).

In the late 1970's, the chemical sensitization of photographic AgBr-polyvinyl alcohol (PVA) emulsions with Au(I) complexes of sulfur or phosphorous-containing ligands was investigated (Suss, Schroter, Reinhold, Zwanziger, and Hoyer, "Gold Sensitization of Silver Bromide Layers in Polyvinyl Alcohol on Glass," *J. Signal AM* 5 (1977) and Hartung, Schroter, Reinhold, Zwanziger, Dietzsch, and Hoyer, "Chemical Sensitization of Photographic Silver Bromide-Polyvinyl Alcohol Emulsions with Gold(I) Complexes of Sulfur or Phosphorus-Containing Ligands," *J. Signal AM* 58 (1980)). In the earlier of these two papers, literature values of standard reduction potentials were shown to correlate, within certain limits, with a given complex's ability to chemically sensitize AgBr in a PVA matrix. In the second paper, polarographic half-wave potentials obtained in acetonitrile were used to experimentally verify the relationship between the ease of electrochemical reduction of a complex and its tendency to chemically sensitize.

While concentrating on the mechanistic relationship between electrochemical reduction potentials and gold (I) chemical sensitization, neither of these aforementioned studies investigated water-soluble gold (I) complexes nor related the stability of the complex in aqueous solution to photographic usefulness. The inventors herein have discovered a method which permits the establishment of a "utility window" of electrochemical potentials which permits the complex to be screened for practical manufacturing suitability.

Such a method for easily and accurately screening gold chemical sensitizers is needed to avoid time consuming and costly experimentation in evaluation such compounds.

SUMMARY OF THE INVENTION

This invention provides a method of screening a water soluble gold complex for use as a sensitizer in a silver halide photographic element comprising experimentally measuring the electrochemical potential of the gold complex and then determining if the electrochemical potential falls within a predetermined utility window.

The screening method of this invention is a fast and accurate method to determine whether specific water soluble gold complexes will be effective as gold sensitizers for silver halide photographic elements. This invention further provides a proven predetermined utility window which may be utilized during the assessment of the gold complexes.

DETAILED DESCRIPTION OF THE INVENTION

In this invention a utility window has been defined in which water soluble gold complexes are effective as chemical sensitizers for silver halide emulsions. Specifically, the electrochemical potential at which Au(0) is formed from solutions of various Au(I) complexes was determined and correlated with each complex's solution stability and ability to sensitize AgX microcrystals within a gelatin matrix (emulsion) in commercial photographic formulations. Ultimately, a "utility window" of potentials was defined which can be used to screen potential Au(I) sensitizers. The effective utility window is about −380 mV to −850 mV, with −407±34 mV to −833±13 mV being preferred. (Potentials are reported versus a standard calomel (Hg/Hg$_2$Cl$_2$), or SCE, reference electrode.)

In order to practice the invention, the electrochemical potential of a water-soluble gold complex is experimentally determined. The electrochemical potential can then be compared to the predetermined utility window to determine whether the gold complex will be useful as a chemical sensitizer.

Several standard electrochemical methodologies may be used to determine characteristic redox potentials for the reduction of the Au(I) complexes. These include voltammetry at stationary and moving electrodes, potentiometry, chronoamperometry, as well as other less common eletrochemical methodologies. In general, the electrochemical apparatus includes an electrochemical cell composed of a working electrode, a reference electrode, and, in cases where current is passed through the cell, an auxiliary electrode. The instrumentation used is a standard potentiostat, such as the EG&G Princeton Applied Research Model 173/179.

Silver halides are electronic insulators, therefore, it is not possible to perform electrochemistry directly on bulk-like silver halide surfaces. Preferably the electrochemical potential is measured in an aqueous system using a platinum, carbon, mercury, gold or other electrochemically inert, but conductive electrode. To avoid possible complications associated with the plate out of dissimilar metals it is most preferable that the electrochemical potential of gold (I) chemical sensitizers be measured in an aqueous system with a gold electrode.

It is well known that the mechanism of deposition of metals onto an electrode is highly sensitive to both solution and surface conditions. While a variety of electrolytes may be used for the reduction of the gold complexes, for example unbuffered KCl, KClO$_4$, KF and KNO$_3$ solutions, after a long investigation it has been determined that a sulfate electrolyte is preferred. Na$_2$SO$_4$ is the most preferred electrolyte for this invention. The electrolytes must be chemically inert: they must be free of interferences i.e. anything that will affect the kinetics of the experiment.

The following examples are intended to illustrate but not to limit the embodiments of this invention.

EXAMPLES

Au(I) Complexes

The voltammetries of five Au(I) complexes were investigated during the course of this work. These compounds included:

1. Gold(I), bis(tetramethylthiourea-S)-, fluoroborate (1-) [Au(TT)$_2$]$^+$:

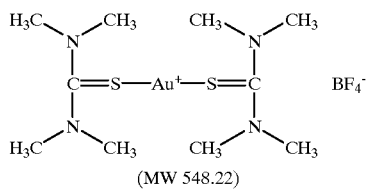

(MW 548.22)

2. Gold(I), bis( 1,4,5-trimethyl-1,2,4-triazolium-3-thiolate-S)-, fluoroborate(1-) [Au(TTT)$_2$]$^+$:

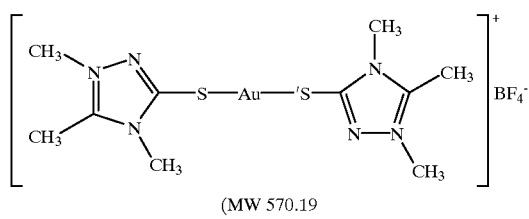

(MW 570.19)

3. Gold(I), bis{1-[3-(2-sulfonatobenzamido)phenyl]-5-mercaptotetrazole tripotassium salt} pentahydrate [Au(SBMT)$_2$]$^{-3}$:

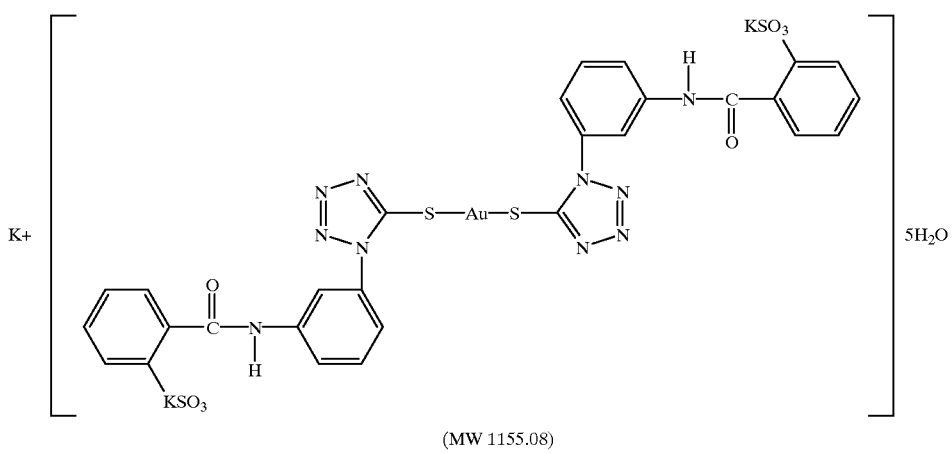

(MW 1155.08)

4. Sodium dithiosulfatoaurate dihydrate [Au(S$_2$O$_3$)$_2$]$^{-3}$:

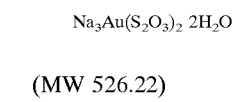

(MW 526.22)

5. Triethylphosphine-gold chloride [Au(TEP)]:

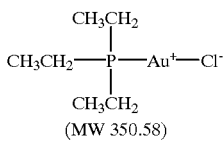

(MW 350.58)

These complexes readily dissolved in the aqueous 0.1 M $Na_2SO_4$ electrolyte used in this study (vide infra). Solutions of $K_3Au(SBMT)$ had to be warmed for several minutes at ca. 30–35° C. before the all of the solid disappeared. In this work, all of the compounds were run within 15 minutes of solution preparation.

Electrochemical Methods

Rotating disk (gold) electrode ($RDE_{Au}$) voltammetry was chosen because of the ease of analysis of polarographic-type curve shapes in differentiating between surface and diffusion-controlled reactions and the direct graphical extraction of characteristic half-wave potentials, $E_{1/2}$. As described previously, the electrochemical instrumentation was of conventional three-electrode design. A Pine Instruments rotator (Model PIR) was used to control the angular velocity ($\omega = 2\pi f$) of the $RDE_{Au}$.

The current in an electrochemical redox reaction is directly proportional to electrode area, A, therefore, a single gold disk electrode [geometrical area: 0.0730 cm²; 99.999% (metals)] was used for all experiments to help normalize the voltammograms for comparisons. Before each experiment, the surface of the gold electrode was prepared using Buehler Ltd. metallographic diamond polishing pastes. The final mechanical surface finishing was performed with 1 μm compound (P/N 40-6128) and water-soluble extender (P/N 406032). The cleanliness of the system was verified by the characteristic curve of the gold electrode in a sulfate electrolyte.

For the complexes investigated and under the conditions used in these experiments, the reductions of the gold complexes to metallic gold are highly irreversible, resulting in the deposition, or "plate out" of metallic gold onto the surface of the $RDE_{Au}$.

$$AuL_2^{1-2n} + e^- \rightarrow Au^o\downarrow + 2L^{-n} \quad n=0,1,2 \quad (2)$$

Open circuit, or zero current potentials, $E_{o,c}$, were obtained 5 minutes after the pre-cleaned electrode was exposed to the electrolyte containing the complex of interest. At least three voltammograms were obtained for each complex.

Results

Table 1 is a compilation of the experimentally-determined electrochemical parameters of interest for comparison of the five Au(I) complexes listed above. The data in Table 1 are the means ($\chi$) and associated standard deviations ($\sigma$) obtained from averaging the results from at least three sets of voltammograms (vide infra) for each complex.

TABLE 1

| Compound | $E_{1/2}$ (mV)* |
|---|---|
| $Au(TT)_2BF_4$ | −283 ± 24 |
| $Au(TTT)_2BF_4$ | −407 ± 34 |
| $Na_3Au(S_2O_3)_2 \cdot 2H_2O$ | −457 ± 33 |
| $K_3Au(SBMT)_2 \cdot 5H_2O$ | −833 ± 13 |
| Au(TEP) | −1380 ± 22 |

*To convert to SHE (standard hydrogen electrode), add 200 mV

Individual Complexes

This section of the results largely involves qualitative evaluation of the electrochemical behaviors of the complexes investigated in this study.

$Au(TT)_2^+$

Under the experimental conditions chosen, this complex yields the most positive E (−283±24 mV) in the series. The experimental voltammograms obtained with this complex typically displayed comparatively little hysteresis (≦10 mV) between the negative-going (forward) and positive-going (reverse) scans in the charge-transfer limiting region of the curves.

After a few cycles in the potential range gold deposits were clearly visible as a dark brown film which uniformly covered the surface of the gold disk electrode. This film could be partially removed by wiping the electrode surface across a metallographic-grade polishing cloth. However, complete removal required additional mechanical polishing with diamond polishes.

UV-visible spectrophotometry was used to investigate the solution stability of the complex $Au(TT)_2BF_4$. A $3.32\times10^{-5}$ M aqueous doctor solution was prepared by dissolving 0.0182 g of the complex in 500.0 mL of high purity water and then passing the solution through a 0.2 μm nylon filter. The solution was transferred into a 1 L translucent polyethylene bottle and diluted to a final volume of 1000.0 mL. The clear and colorless doctor solution was sealed with a polypropylene cap and stored under ambient temperature and light conditions.

The UV-visible spectra of the $Au(TT)_2BF_4$ solution were collected on a Varian Cary 1 Bio UV-visible spectrophotometer operating in the dual beam mode using 1-cm cuvettes. The sample cuvette was rinsed 3 times with the doctor solution prior to data collection. Spectra were collected between 450 nm and 300 nm over the course of 16 days.

$Au(TT)_2$ is considered to be unsuitable for chemical sensitization of photographic emulsions in production due to its limited solution stability. To demonstrate this behavior, the UV-visible spectra of the complex are shown below For quantitative comparison, the absorbance intensities are shown in Table 2 at λ=246.5 nm over the course of 16 days.

TABLE 2

UV-Visible Stability Study of $Au(TT)_2^+$

| Day | Absorbance | % Change |
|---|---|---|
| 1 | 1.223 | 0 |
| 3 | 1.228 | 0.40 |
| 6 | 1.255 | 2.62 |
| 9 | 1.303 | 6.54 |
| 14 | 1.363 | 11.5 |
| 16 | 1.384 | 13.2 |

The spectrum obtained on day 1 shows two absorption maxima at 235 nm ($\epsilon=4.912\times10^4$) and 264 nm ($\epsilon=3.832\times10^4$). The doctor solution was colorless between days 1 and 3. However, on day 6 a pink film due to colloidal gold was observed on the inside surface of the polyethylene bottle. At this point in the experiment, a noticeable change in the UV-visible spectrum of the solution was also apparent. The decomposition of the doctor solution continued through day 16 as evidenced by an increase in the intensity of the gold film and the emergence of a maximum (λ=246.5 nm) in the spectrum. Two isosbestic points are observed at 238 nm and 261 nm, which suggests that the only chromophores in solution are the starting complex and a single organic degradation product.

$Au(TTT)_2^+$

Like $Au(TT)_2^+$, this complex also produces relatively well-behaved voltammograms which reflect the deposition of metallic gold onto the electrode surface during the reduction of the complex. The $E_{1/2}$ potentials are more negative than those obtained for Au(TT)2+, −407±34 mV.

Au(SBMT)$_2^{-3}$

The voltammogram of Au(SBMT)$_2^{-3}$ displays more irreversibility between the forward and reverse scans that those obtained with Au(TT)$_2^+$ and Au(TTT)$_2^+$ (FIG. 5; cf. FIGS. 2 and 4). The displacement between the two scan directions in the charge-transfer region is on the order of 80 to 100 mV, with the positive-going (reverse) scan the more positive of the two.

Following predictions of ease of reducibility based on complex stabilities, the average E of the voltammograms of Au(SBMT)$_2^{-3}$ occurs at a more negative potential, E$_{1/2}$=−833±13 mV, than either Au(TT)$_2^+$ or Au (TTT)$_2^+$, cf. Table 1.

Au(S$_2$O$_3$)$_2^{-3}$

For comparison purposes. The reduction of aurous dithiosulfate [Au(S$_2$O$_3$)$_2$]$^{-3}$ involves multiple redox reactions which yield complex voltammograms. Considerable (~400 mV) potential offset between the forward and reverse waves indicates that the redox processes are different depending on the species at the electrode surface. The steady state voltametric wave at E$_{1/2}$=−457±33 mV is attributed to the reduction of Au(I) and is only visible in the positive-going scan following the large surface wave. For both Au(SBMT)$_2^{-3}$ and Au(S$_2$O$_3$)$_2^{-3}$ the E$_{1/2}$'s from the positive-going scans were used in Table 1 for comparison among the compounds investigated in this study.

Au(TEP)

Triethylphosphine-gold chloride [Au(TEP)] was included in this series as a relatively stable reference Au(I) complex. As such, it was predicted to have the most negative reduction potential of the series. These predictions reflect earlier photographic testing that eliminated this complex as a possible chemical sensitizer due to its lack of influence on the sensitometric curves of several test emulsions.

The RDE$_{Au}$ voltammogram for Au(TEP) were done in 0.1 M Na$_2$SO$_4$. The wave for the reduction of this complex (E$_{1/2}$=−1380±22 mV) nearly coincides wit h the background reduction of hydrogen at −1850 mV. This wave is only observable on t he positive-going scan of the cycle.

Discussion

If the ability of a particular Au(I) complex to chemically sensitize AgX is related to producing surface deposits of Au(0), then the ordering of a complex based on its relative ease of reduction with respect to others in this study is:

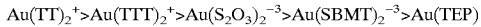

Au(TT)$_2^+$>Au(TTT)$_2^+$>Au(S$_2$O$_3$)$_2^{-3}$>Au(SBMT)$_2^{-3}$>Au(TEP)

In other words, Au(TEP) is a more stable Au(I) complex than Au(TT)$_2^+$. Therefore, Au(TT)$_2^+$ would be expected to more rapidly deposit Au(0) or to metathesize to "AuX" at the surface of AgX than the other complexes investigated. This observation is consistent with the fact that solutions of Au(TT)$_2^+$ are capable of sensitization. However, as shown in Table. 3 the solution stability of Au(TT)$_2^+$ is short-lived compared with production requirements, which are on the order of 7 days. Conversely, a doctor solution of Au(TEP) exhibits an extended shelf life, but fails to sensitize AgX. The three remaining complexes are known AgX chemical sensitizers and possess shelf lives that are sufficiently long to satisfy production requirements.

With the exception on of Au(S$_2$O$_3$)$_2^{-3}$, all of the Au(I) complexes investigated exhibited relatively well-behaved voltammeties at the RDE$_{Au}$. As expected, all undergo highly irreversible one-electron reductions to Au$^\circ$ which results in the plate out of metallic gold on the surface of the electrode.

Coupled with the present electrochemical results from Table 1, these observations suggest that using the experimental approach herein, the reduction of currently known photographically-useful Au(I) sensitizers falls within a potential range of E$_{1/2}$'s 1 between ca. −407±34 mV and −833±13 mV versus SCE.

Hirsch has complied the standard electrode potentials of several Au(I) complexes as shown in Table 3. These potentials cover a potential range, ΔE, of 1.634 V. A comparison of the range of potentials covered by the photographically-useful complexes in this work, ΔE$_{1/2}$=426±47 mV suggests that the class of photograpically-useful Au(I) complexes is defined by a relatively narrow potential range, or "utility window".

TABLE 3

Standard Electrode Potentials of Au(I) Complexes (25° C.)

| Ligand | E° (V vs. SHE) |
|---|---|
| Cl$^-$ | 1.154 |
| Br$^-$ | 0.959 |
| methionine | 0.840 |
| histidine | 0.663 |
| CNS$^-$ | 0.662 |
| I$^-$ | 0.578 |
| NH$_3$ | 0.563 |
| CNSe$^-$ | 0.41 |
| (NH$_2$)$_2$CS | 0.380 |
| S$_2$O$_3^{2-}$ | 0.153 |
| dpm | 0.053 |
| CN$^-$ | −0.48 |

The invention has been described in detail with particular reference to certain preferred embodiments thereof, but it will be understood that variations and modifications can be effected within the spirit and scope of the invention.

What is claimed is:

1. A method of screening a water soluble gold complex for use as a chemical sensitizer in a silver halide photographic element comprised of experimentally measuring the electrochemical potential of the gold complex and then comparing the measured value to a predetermined utility window of −380 mV to −850 mV versus SCE to determine if the electrochemical potential falls within the predetermined utility window.

2. The method of claim 1 wherein the predetermined utility window is −407±34 mV to −833±13 mV versus SCE.

3. The method of claim 1 wherein the electrochemical potential is measured in an aqueous system using a platinum, carbon, mercury or gold electrode.

4. The method of claim 3 wherein the electrochemical potential is measured using a gold electrode.

5. The method of claim 3 wherein the electrochemical potential is measured in an aqueous system using a electrochemically-inert electrolyte.

6. A method of screening a water soluble gold complex for use as a chemical sensitizer in a silver halide photographic element comprised of experimentally measuring the eletrochemical potential of the gold complex and then comparing the measured value to a predetermined utility window to determine if the electrochemical potential falls within the predetermined utility window; wherein the electrochemical potential is measured in an aqueous system using a sulfate electrolyte and a gold electrode.

7. The method of claim 6 wherein the sulfate electrolyte is Na$_2$SO$_4$.

8. The method of claim 7 wherein the predetermined utility window is −407±34 mV to −833±13 mV.

9. The method of claim 6 wherein the predetermined utility window is 380 mV to −850 mV versus SCE.

10. The method of claim 6 wherein the predetermined utility window is −407±34 mV to −833±13 mV.

* * * * *